United States Patent [19]
Broughton et al.

[11] Patent Number: 5,695,486
[45] Date of Patent: Dec. 9, 1997

[54] LIGHT-WEIGHT, LOW DENSITY ABSORBENT STRUCTURE AND METHOD OF MAKING THE STRUCTURE

[75] Inventors: Denise H. Broughton, Cordova; Charles E. Bost, Germantown, both of Tenn.; Howard L. Schoggen, Southaven, Miss.

[73] Assignee: Buckeye Cellulose Corporation, Memphis, Tenn.

[21] Appl. No.: 530,513

[22] Filed: Sep. 19, 1995

[51] Int. Cl.$^6$ .............................. A61F 13/15; A61F 13/20
[52] U.S. Cl. .................... 604/374; 604/365; 604/367; 428/236
[58] Field of Search .................. 604/358, 365, 604/367, 374–375, 372, 368; 428/196, 236, 288

[56] References Cited

U.S. PATENT DOCUMENTS

| | | |
|---|---|---|
| H1565 | 7/1996 | Brodof et al. .................. 604/368 |
| 3,301,746 | 1/1967 | Sanford et al. . |
| 4,536,432 | 8/1985 | Holtman .................. 604/374 |
| 4,673,402 | 6/1987 | Weisman et al. . |
| 4,737,582 | 4/1988 | Goldman et al. . |
| 4,765,780 | 8/1988 | Augstadt . |
| 4,859,527 | 8/1989 | DiStefano . |
| 5,069,677 | 12/1991 | Sakurai et al. . |
| 5,091,240 | 2/1992 | Kajander et al. . |
| 5,167,764 | 12/1992 | Nielsen et al. . |
| 5,171,309 | 12/1992 | Gallacher et al. . |
| 5,171,391 | 12/1992 | Chmielewski et al. . |
| 5,246,429 | 9/1993 | Poccia et al. . |
| 5,248,309 | 9/1993 | Serbiak et al. . |
| 5,281,208 | 1/1994 | Thompson et al. . |
| 5,368,918 | 11/1994 | Harada et al. . |
| 5,378,528 | 1/1995 | Makoui et al. . |
| 5,384,189 | 1/1995 | Kuroda et al. . |
| 5,466,513 | 11/1995 | Wanek et al. . |

OTHER PUBLICATIONS

Article from "Nonwovens World," Bither, Thermally Bonded Absorbent Pads—The Next Generation, Nov. 1986.

*Primary Examiner*—P. Zuttarelli
*Attorney, Agent, or Firm*—Baker, Donelson, Bearman & Caldwell

[57] ABSTRACT

A light weight, low density absorbent structure suitable for use in disposable absorbent products which is formed from a fibrous web of cellulose and cellulose acetate fibers. The fibrous web is treated with a triacetin solvent and heat cured to bond the fibers. The absorbent structure has excellent structural integrity and an absorbent capacity and strength which is equal to or exceeds that of absorbent structures having twice the basis weight.

12 Claims, 2 Drawing Sheets

LIGHT-WEIGHT, LOW DENSITY ABSORBENT STRUCTURE AND METHOD OF MAKING THE STRUCTURE

FIELD OF THE INVENTION

The present invention relates to fibrous webs which are suitable for use in products designed to absorb and retain body fluids, such as diapers, catamenials, and wound dressings. More specifically, the invention provides a light-weight, low-density absorbent structure formed from man-made fibers based on cellulose and cellulosic fibers. The fibers are treated with a chemical solvent and heat-cured to bond the fibers. The solvent treated absorbent structure of the present invention retains the absorbent capacity, fluid transport properties, and strength of known structures having at least twice the basis weight.

BACKGROUND OF THE INVENTION

A wide variety of absorbent structures for use in disposable absorbent articles are known in the art. Common commercial absorbent articles include diapers, adult incontinence products, catamenials and bandages. These products are provided with various functional components for receiving, absorbing and retaining fluids. As consumer demand for less expensive and less bulky disposable absorbent products increases, manufacturers continue to seek effective ways to reduce size and cost without sacrificing the quality of the fluid transport properties or structural integrity of the products during use. Efforts to improve disposable absorbent articles include changes in the barrier films and the geometric configuration of the products, as well as changes in the composition of the absorbent components of the products. Recently, ultrathin products have appeared on the market which incorporate acquisition layers formed from expensive cross-linked cellulose fibers or low density synthetic nonwovens to provide improved fluid transport properties. Nevertheless, due to a high absorption capacity and low cost, most manufacturers continue to favor natural cellulose fibers and super absorbing polymers as the principal absorptive components in the core of disposable absorbent products.

As is well known in the art, cellulose fibers are typically utilized in the form of fibrous webs, which are manufactured by conventional wet-laid techniques. The fibrous webs then are used in air-laid systems to form absorbent structures used as a component of disposable absorbent products. The absorbent structures may vary considerably in weight, density, and composition, depending upon the properties required for a particular type of absorbent product. For example, superabsorbents may be added to enhance the absorbent capacity of the structure, and various synthetic or modified cellulose fibers may be combined with the cellulose fibers in order to achieve a desired characteristic.

In an air-laid process, the fibers are suspended in a stream of air and conveyed to a forming screen where the fibers are condensed into a web. However, at this stage, the fibrous web lacks any significant structural integrity. Often, sheets of tissue are used on the top and bottom of the web to provided additional support to the web. Other means of stabilizing an air-laid web include thermal bonding by including specially treated synthetic fibers which melt upon heating and solidify upon cooling to bond with the cellulose fibers and promote retention of a desired shape. The use of latex binders within and on the surface of fibrous webs also has been proposed as a means to provide structural integrity to fibrous webs. While prior art methods may enhance the structural integrity of some absorbent products, most often these techniques result in a significant reduction in the absorption capacity, wicking rate, and other fluid transport properties which are critical to the effectiveness of an absorbent structure.

Prior to the present invention, webs produced from cellulose fibers were somewhat bulky since the webs had to be of sufficient weight and density to provide minimally acceptable fluid transport properties. Moreover, absorbent structures formed from sufficiently dense cellulosic fibers tend to lose integrity and shape as the structure absorbs fluids. Accordingly, there remains a need for a low bulk absorbent structure made primarily from cellulose fibers which maintains its structural integrity upon saturation without loss of other significant fluid transport properties. Further, it is desirable to provide a method for producing an improved absorbent structure which does not require substantial modifications of the equipment or processes currently employed by commercial manufacturers of disposable absorbent products.

SUMMARY OF THE INVENTION

The present invention satisfies these and other needs by providing a light-weight, low-density absorbent structure which is particularly suitable for use as a component in disposable absorbent products. Surprisingly, it has been discovered that when the surface of a web formed from a combination of cellulosic and cellulose-based man-made fibers is treated with a chemical solvent and heat cured to bond the fibers, the resulting absorbent structure exhibits exceptional strength at half or less of the basis weight of untreated standard absorbent structures formed from only cellulose fibers, while retaining or enhancing the superior fluid transport properties which are characteristic of cellulose fiber webs. In addition, the method of the present invention can be easily incorporated into manufacturing systems currently utilized to produce a variety of disposable absorbent products without substantial modifications to the equipment or the process.

Conventional wet-laid techniques may be used to combine the cellulose and cellulose-based man-made fibers to form standard webs or sheets. The sheets may then be fed through conventional air laying systems to form a fibrous layer having a desired weight and density. Alternately, the cellulose-based man-made fibers may be dry blended with the cellulose fibers to form a fluff which is then fed through conventional air laying systems to form the fibrous layer. At least one surface of the fibrous layer then is treated with a chemical solvent and subjected to a heat curing step to bond the cellulose-based man-made fibers to the cellulose fibers. The absorbent structure prepared by the method of the present invention exhibits exceptional strength and fluid transport ability at half or less of the basis weight of untreated standard absorbent structures containing only cellulose fibers.

Preferably, the fibrous portion of the absorbent structure of the present invention is formed from between about 85% to about 95% by weight of cellulose fibers and between about 5% to 15% by weight of cellulose acetate fibers.

In a preferred embodiment, the fibrous portion of the present absorbent structure is composed of between about 88% and about 92% by weight of cellulose fibers and between about 8% and about 12% by weight of cellulose acetate fibers. In a particularly preferred embodiment, the fibrous potion of the absorbent structure comprises about 90% cellulose fibers and about 10% cellulose acetate fibers by weight. Conventional air laying techniques are used to form an absorbent layer having a density of between about 0.03 g/cc and 0.15 g/cc and a basis weight of between about 150 g/m² and about 1,000 g/m².

After forming an absorbent layer of the desired density and weight, a cellulose acetate solvent is applied to the layer. Most preferably, the solvent is 100% triacetin. The triacetin is applied in an amount of between about 2% and about 14% by weight of the total amount of bone dry fiber in the layer. The cellulose acetate solvent may be applied by spraying one or both surfaces of the absorbent layer, by pulling the solvent through the layer in the form of a mist, or by any method which evenly distributes small amounts of the solvent throughout the absorbent layer. The solvent treated absorbent layer is then heat cured by passing the layer through a hot air oven or an air drier at a temperature sufficient to bond the cellulose acetate fibers. After curing, the absorbent structure of the present invention has a drip capacity of at least 20 ml/g and a burst strength of at least 200 g.

The solvent treated absorbent structure of the present invention may be utilized as a single layer or combined with one or more additional solvent treated absorbent structures to form a layered component for use in a disposable absorbent product. Moreover, as is known in the art, superabsorbents or other additives may be combined with the cellulose and cellulose acetate fibers prior to solvent treatment, depending upon the desired characteristics of the final absorbent product. The solvent treated absorbent structure of the present invention also may be combined with other functional components to form a disposable absorbent product. For example, the solvent treated absorbent structure of the present invention may serve as the fluid storage layer in a disposable diaper, while a layer having a different structure and composition is used as the fluid acquisition and distribution layer.

DETAILED DESCRIPTION OF THE INVENTION

Figure 1:
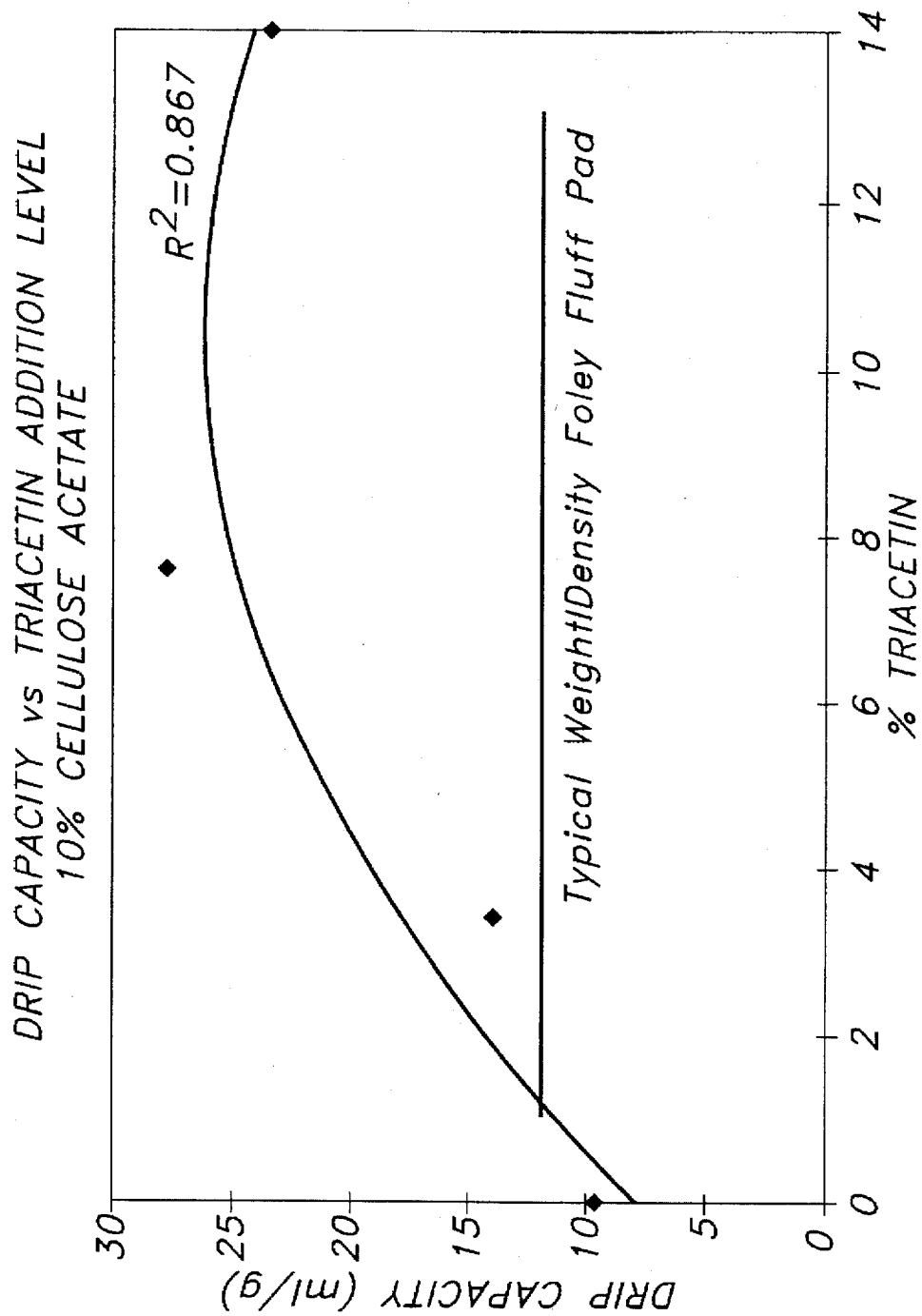
FIG. 1 is a graphic presentation of the effects of varying amounts of triacetin on the drip capacity of absorbent structures prepared according to the method of the present invention.

The absorbent structure of the present invention is formed by combining cellulose fibers with cellulose acetate fibers and compressing the fibers into a layer of desired density using standard airlaying techniques. The fibrous layer is treated with triacetin and heat cured to bond the cellulose and cellulose acetate fibers. The resulting light-weight low density structure has exceptional fluid transport properties, a high absorption capacity, and excellent structural integrity upon saturation with fluids.

The cellulose fibers used in the present absorbent structure may be cotton linters, CTMP, northern or southern softwood fibers or hardwood blends. Chemically pulped wood fibers, such as southern softwood fibers, are especially suitable for use in the absorbent structure of the present invention. In a particularly preferred embodiment, the cellulose fibers are chemically pulped southern softwood fibers sold by Buckeye Cellulose Corporation, 1001 Tillman Street, Memphis, Tenn. 38108, under the tradename FOLEY FLUFF.

The cellulose acetate fibers used in the absorbent structure of the present invention may be produced from cellulose acetate tow. Preferably, the cellulose acetate fibers have a length of between about ⅛ and ¼ inches and a denier of between about 1.7 and 2.7 dpf. Suitable cellulose acetate tow is available from Hoechst Celanese Corporation, 2300 Archdale Drive, Charlotte, N.C. 28210; Rhone-Poulenc, 25, Quai Paul Doumer, 92408 Courbevoie Cedex, Paris, France; Tennessee Eastman Division, Eastman Chemical Company, P.O. Box 511, Eastman Road, Kingsport, Tenn. 37662; Daicel Chemical Industries, Ltd., 8-1 Kasumigaseki 3-Chome, Chiyoda-ku, Tokyo, 100 Japan; and Courtaulds plc, 50 George Street, London W1A2BB, England.

Although any solvent which will bond the cellulose acetate fibers to the cellulose fibers may be used in the present method, the preferred solvent has a low toxicity and is effective at low concentrations. In a particularly preferred embodiment, 100% triacetin is used as the solvent for the cellulose acetate in the present absorbent structure. Typically, the solvent is applied to at least one surface of the absorbent structure by conventional spraying techniques. However, the solvent may be applied by any suitable alternate method may be utilized to apply the solvent to the fibrous layer.

After application of the solvent, the absorbent structure is heat cured to bond the cellulose acetate to the cellulose fibers. Any conventional means for heat curing is suitable for use in the present method. However, in order to achieve acceptable bonding, it is desirable to heat the solvent treated absorbent structure to a temperature of at least 74° C.

In order to demonstrate the superior fluid capacity and structural integrity of the present light-weight, low-density absorbent structure, comparative tests were conducted which measure the drip capacity and burst strength of absorbent structures prepared according to the present method and treated with varying amounts of triacetin. The experimental data show that the present solvent treated absorbent structures exhibit a drip capacity which is equal to or greater than the standard 100% cellulose control structures having a significantly higher density and basis weight. The data also shows that the present absorbent structure has strength at least equal to or greater than a standard 100% cellulose control structure having twice the basis weight.

Preparation of Standard Control Structures

The cellulose fibers used in the standard control pads were provided as machine sheeted 100% cellulose pulp obtained from Buckeye Cellulose Corporation. The dry, machine sheeted pulp was converted into a fluff form which did not contain a large quantity of fiber clumps by cutting the pulp into 1"×4" strips with the 4" dimension in the machine direction. The strips were individually fed into a fluffer at a consistent rate of about 1 strip every four seconds to produce a uniform fluff.

A laboratory scale padmaker which duplicates the commercial padforming process was used to air lay the dry uniform fluff into pads in a conditioned environment. In order to overcome the effects of disintegrating the pulp in an unconditioned atmosphere and expose the pads to the conditioned environment, the pads were allowed to remain in the padmaker for 4–5 minutes with the compressed air off and the vacuum on. Additionally, this procedure overcomes the possible effect of the compressed air used in padmaking not being at 50% relative humidity.

A ply of tissue which measured 14½"×14½" was placed on the forming screen of the padmaker. The tissue completely covered the forming screen and curved up the sides. This tissue represents the bottom side of the airlaid felt pad. Fifty-two grams of the fluff sample was added to the padformer in four equal increments to form a uniform pad. After the fluff was added to the air-laid pad, the forming screen was removed with the pad on it and carefully transferred to a smooth, flat surface. A second covering tissue was marked to indicate the top side of the airlaid felt pad and placed on top of the pad, making sure that the machine direction of the second tissue ply is in the same direction as that of the first ply. A weight which measured 14"×14" was placed on the pad in a manner which did not disturb the formation of the pad. The weight was allowed to remain on the pad for a minimum of 5 minutes and then carefully removed.

The pad was cut into a 12¾"×12¾" square by removing approximately the same from each edge with a standard paper cutter board. This pad was cut into nine square pads which measured 4¼"×4¼" each. Each pad weighed about 4.75 grams, which represented 4.25 grams of fluff and 0.50 grams for the two cover sheets. The airlaid felt pads were then stored in an area maintained at 23°±1° C.(73.4°±2° F.) and 50±5% relative humidity until needed for testing.

The covering tissues on the 4¼"×4¼" pad were carefully removed and the pad was placed on the bottom half of an aluminum press plate. The press plate is made from two blocks of aluminum measuring 6"×6"×1". One 6"×6" face of each block was machined to a perfectly flat surface. Aligning pins are fixed near two corners of one plate. Corresponding holes are formed in the other plate for receiving the pins. The top half of the press plate was placed over the pad to pressed and the entire press plate was placed on a Carver hydraulic press (Model No. 16600-224). Each pad was pressed at the appropriate pressure to produce the desired density. Since the size of the pad increased as a result of pressing, the pad was trimmed to measure 4"×4" each and weighed. After waiting 120 seconds for delayed rebounding, the thickness of each pad was measured. The density of the pad was then calculated according to the following formula:

$$\text{Density in grams/cc of a 4"} \times 4\text{" pad} = \frac{0.00379 \times \text{weight (gms)}}{\text{thickness (inches)}}$$

Procedure For Drip Capacity Test

In order to demonstrate the fluid transport capability of the absorbent structure of the present invention to retain fluids at a lower density and basis weight, airlaid experimental pads were prepared according to method of the present invention. Standard pads which contained 100% cellulose fibers were prepared according to the procedure described above for use as control pads. The fluid transport capability of each pad was measured by determining the drip capacity in milliliters of liquid per grams of cellulose in a pad without covering tissues.

Synthetic urine was prepared by dissolving 108.4 g of a dry synthetic urine mixture in 20 liters of distilled water. The dry synthetic urine mixture may be obtained from Endovations, Inc., Reading, Pa. A burette was filled with the synthetic urine solution and the flow rate of the pipette was adjusted to deliver 2 mls of urine per second.

The delivery tip on the stopcock of the burette was positioned 1" above and perpendicular to a cube made of 0.5 inch wire mesh. The cube was placed in a pan for receiving the excess fluid. The top face of the cube was maintained in a level position.

Immediately after pressing to the desired density, the pad was placed on the cube so that the fluid impact point is at a crosswire position. Simultaneously, the stopcock on the burette was opened and the timer was started. The synthetic urine was allowed to drip at a controlled rate onto the center of the pad. The timer was stopped when the first drop of liquid was released by the pad and fell into the pan. The time required for the first drop of liquid to pass through the pad was recorded.

The wet pad was removed from the cube and discarded. The cube was dried completely and returned to the pan. The above procedure was repeated on two more pads which were identical to the first in weight, density and composition. The weight, density, and time was recorded for each of the three individual pads. The drip capacity for each pad was calculated according to the following formula:

Drip capacity in milliliters liquid/gram sample =

$$\frac{\text{Time in sec.} \times 2}{\text{Weight (grams) of 4"} \times 4\text{" pad}}$$

The average drip capacity of the three pads was then determined.

Procedure For Burst Strength Test

In order to demonstrate the burst strength of the present absorbent structure at a lower density and basis weight, airlaid experimental pads were prepared according to the method of the present invention. Standard pads which contained 100% cellulose fibers were prepared according to the procedure described above for use as control pads. The burst strength of each pad was determined by measuring the force required for the ball penetrator of a conventional tensile testing apparatus to reach the point of no resistance in a pad without covering tissues.

A Thwing Albert Intelect II tensile tester was used to measure the burst strength of the pads. The tensile tester includes a clamp platform and clamp plate for securing a test pad in a horizontal position between the platform and the plate. The platform and clamp plate are provided with corresponding holes for receiving a ball penetrator which is positioned directly above the holes. The tensile tester was set up in compression mode and attached to a gram cell which monitors any resistance encountered by the ball penetrator. The ball penetrator had a diameter of 1.5 cm.

Immediately after pressing to the desired density, the pad was placed over the hole on the clamp platform, and the clamp plate was securely clamped over the pad to hold the pad in place. The Intelect was started, with the crosshead set to travel downward at 1.0 in/min or 2.54 cm/min. As the ball penetrator moves down and contacts the pad, an ever increasing force measurement shows continuously on the monitor. The penetrator continues to move completely through the pad until reaching the point of no resistance, which is typically when the pad breaks. At this point, the crosshead automatically rebounds upward to the starting position. The maximum force value on the monitor of the Intelect was recorded. This process was repeated two times with new pads. Three pad values were averaged and the maximum force value was reported in grams.

Experimental Example 1

Experimental pads according to the present invention were prepared by wet blending cellulose fibers with cellulose acetate fibers in a disintegrator available from the Technical Association of the Pulp and Paper Industry ("TAPPI"). The cellulose fibers used in the experimental pads were provided as machine sheeted pulp obtained from Buckeye Cellulose Corporation. The cellulose acetate tow fibers used in the experimental pads had a length of ¼" and a denier of 2.7. The fibers were combined in a slurry in a ratio of 90% cellulose to 10% cellulose acetate tow. The fiber slurry was sheeted using a Williams handsheet mold, and then dried on steam drum cans. The dried handsheet was cut into 1"×4" strips which were defiberized in a three stage fluffer to produce a comminuted uniform airfelt.

An airfelt pad measuring 14"×14" and weighing about 75 g/m² was formed by airlaying 13 grams of the fibers in a laboratory scale padformer. This pad was then cut into experimental pads measuring 4¼"×4¼". The surface of one experimental pad was sprayed with 100% triacetin in the amount of 7.6% by weight of the amount of bone dry fiber in the experimental pad. A second experimental pad without triacetin was placed over the triacetin coated surface of the first experimental pad so that the triacetin was layered in the center of the experimental pad. The total pad was heat cured by oven drying at a temperature of 125° C. for about 1 hour. The experimental pad had a basis weight of 160 g/m², which is about 50% less than the basis weight 325 g/m² of a standard 100% cellulose fiber pad. The sandwiched pad was lightly pressed to a target density of 0.03 g/cc and trimmed to precisely 4"×4" using the procedures described above.

Figure 2:
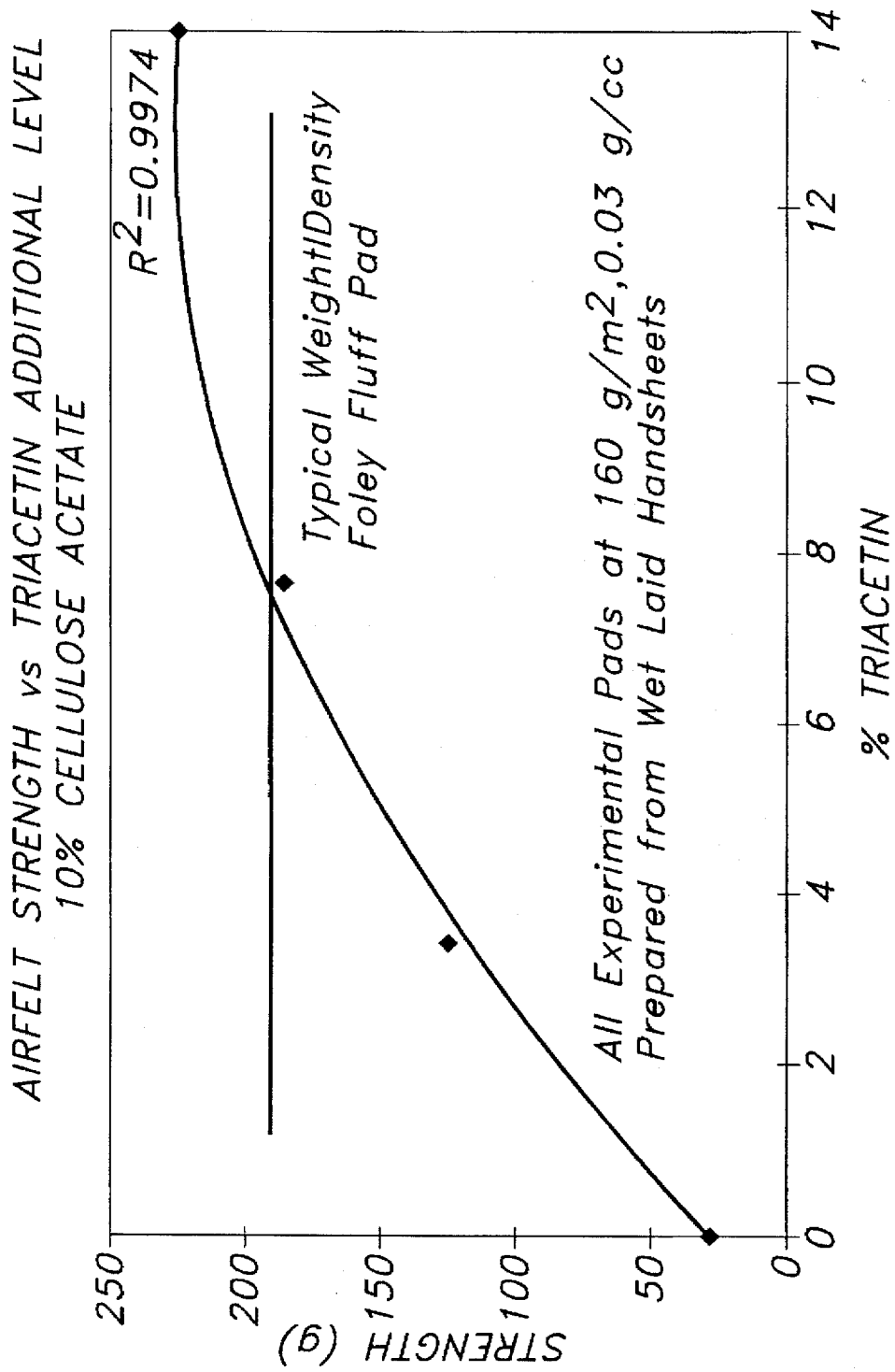
FIG. 2 is a graphic presentation of the effects of varying amounts of triacetin on the strength of the absorbent structures prepared according to the method of the present invention.

The experimental pad was evaluated by the drip capacity and airfelt burst strength tests described above. As shown in FIGS. 1 and 2, the experimental pad prepared according to the method of the present invention had a drip capacity of about 28.2 ml/g and a burst strength of about 123 g. A standard 100% cellulose fiber pad prepared according to the procedure described above has a basis weight of 325 g/m² and a density of 0.10 g/cc, and exhibits a drip capacity of 12 ml/g with a burst strength of 185 g.

Experimental Example 2

Experimental pads were prepared as in Example No. 1 above, but sprayed with triacetin in the amount of 3.4% by weight of the amount of bone dry fiber in the experimental pad. Each experimental pad was tested for drip capacity and burst strength as described in Example 1. As shown in FIGS. 1 and 2, the experimental pads prepared according to the method of the present invention had a drip capacity of 14 ml/g and a burst strength of 122 g.

Experimental Example 3

Experimental pads were prepared as in Example No. 1 above, but sprayed with triacetin in the amount of 14% by weight of the amount of bone dry fiber in the experimental pad. Each experimental pad was tested for drip capacity and burst strength as described in Example 1. As shown in FIGS. 1 and 2, the experimental pad prepared according to the method of the present invention had a drip capacity of 23.6 ml/g and a burst strength of 223 g.

Experimental Example 4

Experimental pads were prepared as in Example No. 1, however, NO triacetin was applied to the pads. The experimental pads were tested for drip capacity and burst strength as described in Example 1. As shown in FIGS. 1 and 2, these experimental pads had a drip capacity of only 9.7 ml/g and a burst strength of only 28.9 g.

Although the invention is described with respect to a preferred embodiment, it is expected that various modifications may be made thereto without departing from the spirit and scope of the invention. Therefore, the scope of the invention is to be determined by reference to the claims which follow.

What is claimed is:

1. An absorbent structure for absorbing, transporting and retaining fluids which comprises:
   cellulose fibers in an amount of between about 85 and about 95 percent of the fibrous basis weight of the structure;
   discontinuous cellulose acetate fibers in an amount of between about 5 and about 15 percent of the fibrous basis weight of the structure; and
   an organic solvent in an amount sufficient to solubilize and bond the cellulose acetate fibers to the cellulose fibers.

2. The absorbent structure of claim 1 wherein the organic solvent is a 100% solution of triacetin.

3. The absorbent structure of claim 2 wherein the triacetin is added in an amount of between about 2% and about 14% by weight of the total mount of bone dry fiber in the absorbent structure.

4. The absorbent structure of claim 1 wherein said cellulose acetate fibers are present in an amount of about 10 percent of the fibrous basis weight of the structure.

5. The absorbent structure of claim 1 which further comprises a predetermined amount of superabsorbent material.

6. An absorbent structure which comprises a dry laid fibrous web formed from a mixture of cellulosic fibers and discontinuous cellulose acetate fibers; and a triacetin solvent, said structure having (i) a basis weight of about 150 to 1000 grams per square meter, (ii) a density of about 0.03 to 0.15 grams per cubic centimeter, (iii) a drip capacity of not less than 20 milliliters per gram of structure, and (iv) a burst strength of not less than 200 grams.

7. The absorbent structure of claim 6 wherein said mixture of cellulose and cellulose acetate fibers is prepared by a dry blending technique.

8. The absorbent structure of claim 6 wherein said mixture of cellulose and cellulose acetate fibers is prepared by a wet blending technique.

9. A disposable diaper containing at least one absorbent structure which comprises a dry laid fibrous web formed from a mixture of cellulosic fibers and discontinuous cellulose acetate fibers; and triacetin, said structure having (i) a basis weight of about 150 to 1000 grams per square meter, (ii) a density of about 0.03 to 0.15 grams per cubic centimeter, (iii) a drip capacity of not less than 20 milliliters per gram of structure, and (iv) a burst strength of not less than 200 grams.

10. A sanitary napkin containing at least one absorbent structure which comprises a dry laid fibrous web formed from a mixture of cellulosic fibers and discontinuous cellulose acetate fibers; and triacetin, said structure having (i) a basis weight of about 150 to 1000 grams per square meter, (ii) a density of about 0.03 to 0.15 grams per cubic centimeter, (iii) a drip capacity of not less than 20 milliliters per gram of structure, and (iv) a burst strength of not less than 200 grams.

11. An absorbent structure which comprises a dry laid fibrous web formed from a substantially uniform mixture of discontinuous cellulosic fibers in an amount of between about 85 and about 95 percent of the fibrous basis weight of the structure and discontinuous cellulose acetate fibers in an amount of between about 5 and about 15 percent of the fibrous basis weight of the structure; and a triacetin solvent in an amount sufficient to solubilize and bond the cellulose acetate fibers to the cellulose fibers, said structure having (i) a basis weight of about 150 to 1000 grams per square meter, (ii) a density of about 0.03 to 0.15 grams per cubic centimeter, (iii) a drip capacity of not less than 20 milliliters per gram of structure, and (iv) a burst strength of not less than 200 grams.

12. An absorbent structure which comprises:

cellulose fibers in an amount of between about 85 and 95 percent of the fibrous basis weight of the structure;

discontinuous cellulose acetate fibers in an amount of between about 5 and 15 percent of the fibrous basis weight of the structure; and an organic solvent in an amount of between about 2% and about 14% by weight of the total amount of bone dry fiber in the absorbent structures for solubilizing and bonding the cellulose acetate fibers to the cellulose fibers.

* * * * *

UNITED STATES PATENT AND TRADEMARK OFFICE
CERTIFICATE OF CORRECTION

PATENT NO. : 5,695,486
DATED : December 9, 1997
INVENTOR(S) : Denise H. Broughton, Charles E. Bost and Howard L. Schoggen It is certified that error appears in the above-indentified patent and that said Letters Patent is hereby corrected as shown below:

In Claim 3, column 8, line 21 please delete "mount"
    and insert --amount--.

Signed and Sealed this

Thirty-first Day of March, 1998

Attest:

BRUCE LEHMAN

Attesting Officer            Commissioner of Patents and Trademarks